(12) United States Patent
Franklin et al.

(10) Patent No.: US 10,806,903 B2
(45) Date of Patent: Oct. 20, 2020

(54) HANDHELD MULTI-NEEDLE VASCULAR ACCESS DEVICE

(71) Applicant: Prytime Medical Devices, Inc., Boerne, TX (US)

(72) Inventors: Curtis J. Franklin, Lakewood, CO (US); Luke William Fisher, Lakewood, CO (US); Elijah Atkinson, Round Rock, TX (US); Todd J. Krummenacher, Lakewood, CO (US); Jonathan L. Eliason, Ann Arbor, MI (US)

(73) Assignee: PRYTIME MEDICAL DEVICES, INC., Boerne, TX (US)

( * ) Notice: Subject to any disclaimer, the term of this patent is extended or adjusted under 35 U.S.C. 154(b) by 486 days.

(21) Appl. No.: 15/627,578

(22) Filed: Jun. 20, 2017

(65) Prior Publication Data
US 2017/0368313 A1 Dec. 28, 2017

Related U.S. Application Data

(60) Provisional application No. 62/353,116, filed on Jun. 22, 2016.

(51) Int. Cl.
*A61M 25/06* (2006.01)
*A61M 5/32* (2006.01)
(Continued)

(52) U.S. Cl.
CPC ........ *A61M 25/065* (2013.01); *A61M 5/3287* (2013.01); *A61M 5/3298* (2013.01);
(Continued)

(58) Field of Classification Search
CPC ............ A61M 25/065; A61M 25/0023; A61M 39/0208; A61M 2025/0188;
(Continued)

(56) References Cited

U.S. PATENT DOCUMENTS 3,964,482 A 6/1976 Gerstel et al.
5,611,809 A 3/1997 Marshall et al.
(Continued)

FOREIGN PATENT DOCUMENTS

FR 2448337 A1 9/1980
KR 20040022824 A 3/2004
(Continued)

OTHER PUBLICATIONS

Int'l Preliminary Report on Patentability dated Sep. 1, 2015 in Int'l Application No. PCT/US2014/018773.
(Continued)

*Primary Examiner* — Lauren P Farrar
(74) *Attorney, Agent, or Firm* — Panitch Schwarze Belisario & Nadel LLP (57) ABSTRACT

A handheld vascular access device for gaining access to a patient's vessel includes a hub, a plurality of access needles and a manifold. The hub has an inner wall and side walls that define a plurality of ports. Each of the plurality of ports has a proximal port end and a distal port end. The proximal port ends define a proximal cross-sectional area and the distal port ends define a distal cross-sectional area. The proximal cross-sectional areas are greater than the distal cross-sectional areas. Each of the plurality of ports taper from the proximal port end to the distal port end. The plurality of hollow access needles is arranged along a plane and fixedly coupled to the distal end of the hub. Each of the plurality of needles has a tip. The manifold removably engages the hub at the proximal end of the hub.

20 Claims, 9 Drawing Sheets

(51) Int. Cl.
    *A61M 25/00*      (2006.01)
    *A61M 39/02*      (2006.01)
    *A61M 25/01*      (2006.01)

(52) U.S. Cl.
    CPC .... *A61M 25/0023* (2013.01); *A61M 39/0208* (2013.01); *A61M 2025/0188* (2013.01)

(58) Field of Classification Search
    CPC ........ A61M 2005/1586; A61M 5/3298; A61M 2025/0087; A61M 5/1408
    See application file for complete search history.

(56) References Cited

U.S. PATENT DOCUMENTS

| | | |
|---|---|---|
| 2002/0045850 A1 | 4/2002 | Rowe et al. |
| 2003/0199823 A1 | 10/2003 | Bobroff et al. |
| 2003/0208167 A1 | 11/2003 | Prausnitz et al. |
| 2003/0229317 A1 | 12/2003 | Ferguson et al. |
| 2008/0177223 A1* | 7/2008 | Johnston ................ A61D 1/025 604/68 |
| 2010/0312173 A1 | 12/2010 | McKay et al. |
| 2010/0330589 A1* | 12/2010 | Bahrami ............ A61M 5/1452 435/7.9 |
| 2011/0004143 A1* | 1/2011 | Beiriger ................ A61M 1/342 604/6.11 |
| 2012/0197214 A1* | 8/2012 | Manley ................ A61M 19/00 604/246 |
| 2014/0243873 A1 | 8/2014 | Franklin |
| 2014/0249504 A1 | 9/2014 | Franklin et al. |
| 2015/0246214 A1 | 9/2015 | Simmers |
| 2016/0114144 A1* | 4/2016 | Sumida ............... A61M 5/3298 604/173 |
| 2016/0213893 A1 | 7/2016 | Franklin |

FOREIGN PATENT DOCUMENTS

| | | |
|---|---|---|
| WO | 9322971 A1 | 11/1993 |
| WO | 2015191685 A1 | 12/2015 |

OTHER PUBLICATIONS

International Search Report and Written Opinion dated May 7, 2014 in corresponding foreign applications PCT/US2014/018773.
Extended Search Report dated Sep. 9, 2016 in EP Appln No. 14756921.4.
Office Action dated May 5, 2016 in U.S. Appl. No. 14/191,236, by Franklin.
Office Action dated Nov. 10, 2016 in U.S. Appl. No. 14/191,236, by Franklin.
Examination Report dated Feb. 3, 2017 in AU Application No. 2014223556.

* cited by examiner

HANDHELD MULTI-NEEDLE VASCULAR ACCESS DEVICE

CROSS-REFERENCE TO RELATED APPLICATIONS

The present application claims the benefit of U.S. Provisional Patent Application No. 62/353,116, filed on Jun. 22, 2016 and titled, "Handheld Multi-Needle Vascular Access Device," the entire contents of which are incorporated herein by reference in their entirety.

STATEMENT REGARDING FEDERALLY SPONSORED RESEARCH OR DEVELOPMENT

This invention was made with government support under Contract No. W81XWH-14-1-0601 awarded by the U.S. Army Medical Research and Materiel Command. The government has certain rights in the invention.

BACKGROUND OF THE INVENTION

The preferred invention generally relates to devices for vascular access. More particularly, the preferred invention relates to handheld devices for assisting medical practitioners in achieving vascular access in a rapid and consistent manner, especially when there is a need for emergency medical intervention at or near the scene of severe injury, such as in battlefield conditions, serious traffic accidents, gunshot wounds, etc., where hospital-like condition usually do not exist or in nearly any situation where a medical practitioner wants to gain access to a patient's vessel relatively quickly and to limit potential failures encountered when attempting access with a single needle. A potential procedure for use of the preferred access device is a resuscitative endovascular balloon occlusion ("REBOA") of the aorta, to maintain blood flow to the heart, brain and other vital organs while diverting blood from less vital organs, like the limbs in the lower portion of the patient's body.

Typically, blood vessels or other hollow organs are accessed by practicing the Seldinger technique. In the Seldinger technique, the desired vessel or cavity is punctured with a sharp hollow needle called a trocar, usually with guidance by ultrasound, fluoroscopy, visual inspection or other imaging to guide the needle placement (hereinafter "needle guidance system") to assure the correct vessel or organ is accessed by the needle. A round-tipped guidewire is then advanced through the lumen of the trocar, and the trocar is withdrawn. A "sheath" or blunt cannula with a dilator can then be passed over the guidewire into the cavity or vessel. After passing a sheath or tube, the guidewire and dilator are withdrawn. Vascular access, such as through the Seldinger technique with a needle guidance system, is generally not practiced outside of controlled hospital environments, and is generally not suitable to uncontrolled environments.

Paramedics, military medics, and other medical professionals who typically practice in field settings rather than clinic or hospital settings generally do not have available ultrasound systems or other needle guidance systems for assisting with vascular access. Even trained vascular surgeons may require ultrasound assistance to properly access the vessel for guidewire placement. Still further, medical professionals in the field or other settings may experience conditions where practicing standard vascular access techniques using needle guidance systems may be impractical, cost prohibitive or impossible.

The invention set forth in U.S. Patent Application Publication No. 2014/0249504 ("'504 publication"), titled "Vascular Access Systems and Methods of Use" and invented by Curtis Franklin and Dr. Jonathan Eliason, is one device designed to overcome the limitations of the traditional Seldinger technique using needle guidance systems. The '504 publication discloses a device that makes use of a portable needle-deploying structure to overcome some of the limitations of traditional vasculature access devices and techniques. The preferred present invention seeks to improve upon the portability and ease of use of such devices as those disclosed in the '504 publication for first responders, battlefield medics, or any other medical personnel dealing with trauma situations or any situation where access to a vessel is desired.

BRIEF SUMMARY OF THE INVENTION

Briefly stated, the preferred vascular access device of the present invention is a handheld device for providing vascular access rapidly and generally without the need for a needle guidance system, such as an ultrasound system. With the inventive vascular access device, vascular access may be achieved by medical professionals in the field or other settings where conditions for practicing standard vascular access techniques, such as the Seldinger technique using a needle guidance system, may be impractical or impossible. The handheld vascular access device of the preferred invention makes it likely that the proper blood vessel can be accessed readily in view of the plurality of hollow access needles and their arrangement and allows for greater manipulation of the device than prior devices.

In one preferred embodiment, the handheld vascular access device of the present invention includes a hub, wherein the hub has a proximal end and a distal end disposed opposite the proximal end. The hub also includes a top wall, a bottom wall disposed opposite the top wall and side walls connecting the top wall and the bottom wall and extending between the proximal end and distal end. An inner wall extends between the proximal end and the distal end. The inner wall defines a plurality of ports extending from the proximal end in the direction of the distal end or that taper from a relatively large diameter at the proximal end toward a smaller diameter as they extend toward the distal end. A plurality of hollow access needles are arranged along a plane and fixedly coupled to the distal end of the hub. Each of the access needles has a first end fixedly coupled to the distal end of the hub and a second end disposed distally of the first end. A removable manifold releasably engages the hub at the proximal end of the hub.

In another aspect, the preferred present invention is directed to the handheld vascular access device, wherein the plurality of needles are evenly spaced from one another (center of needle to center of needle), although this even spacing may not be necessary or desirable in various embodiments. The relatively even spacing of the needles provides optimized lateral spanning of the region of a desired blood vessel (such as the femoral artery or vein, brachial artery or vein or radial artery or vein). While holding the vascular access device at an angle relative to the skin, a medical professional may advance the device such that the hollow access needles penetrate the skin of the patient, preferably simultaneously and evenly, although one or more of the needles of the device may have a different length or be spaced differently from the other hollow access needles of the device if desired. The needles may have different lengths or be unevenly spaced for intended use in different parts of the body where such lengths and spacing address a clinical need. The device may be advanced until aspiration of blood sufficient to indicate vascular access is observed from at least one of the hub's ports. If more than one port is aspirating blood, the port aspirating the most blood has likely accessed the desired blood vessel, such as a large artery, e.g. the femoral artery. Less aspiration would likely be noted in a smaller artery or vein. A guidewire may then be fed through the hub's port, into the aspirating needle, and subsequently into the blood vessel. The vascular access device may then be removed while maintaining the position of the guidewire. The desired blood vessel is thus accessed and ready to have a catheter, sheath, occlusion device, second wire, or other medical device inserted therein, as necessary. By use of the preferred vascular device, vascular access may be rapidly, safely, and repeatedly achieved, without the need for any needle guidance systems. As such, vascular access may be achieved by medical professionals in the field or other settings where conditions for practicing known vascular access techniques, such as when using a needle guidance system may be impractical or impossible. If conditions permit, however, and a needle guidance system is available, the guidance system may be used with the handheld vascular access device of the preferred invention.

In an additional aspect, the preferred invention is directed to a handheld multi-needle vascular access device for gaining access to a patient's vessel. The access device includes a hub having a proximal end, a distal end disposed opposite the proximal end, a top wall, a bottom wall disposed opposite the top wall and side walls connecting the top wall and the bottom wall. The side walls extend between the proximal end and the distal end. An inner wall extends between the proximal end and the distal end. The inner wall and side walls define a plurality of ports extending from the proximal end to the distal end. Each of the plurality of ports has a proximal port end and a distal port end. The proximal port ends define a proximal port end cross-sectional area and the distal port ends define a distal port end cross-sectional area. The proximal port end cross-sectional areas are greater than the distal port end cross-sectional areas. Each of the plurality of ports taper from the proximal port end to the distal port end. A plurality of hollow access needles are arranged along a plane and are fixedly coupled to the distal end of the hub. Each of the plurality of needles has a proximal needle end fixedly coupled to the distal end of the hub and a tip disposed distally of the proximal needle end. A removable manifold removably engages the hub at the proximal end of the hub.

In a further aspect, the preferred invention is directed to

The preferred invention is set forth in part in the description which follows, and in part will be apparent to one having ordinary skill in the art from this description, or can be learned by practice of the invention. The advantages of the device will be realized and attained by means of the elements and combinations particularly pointed out in the appended claims. It is to be understood that both the foregoing general description and the following detailed description are exemplary and explanatory only and are not restrictive of the device as claimed.

BRIEF DESCRIPTION OF THE SEVERAL VIEWS OF THE DRAWINGS

The foregoing summary, as well as the following detailed description of preferred embodiments of the instrument, implant and method of the handheld vascular access device of the present invention, will be better understood when read in conjunction with the appended drawings. For the purposes of illustrating the preferred handheld vascular access device, there are shown in the drawings preferred embodiments. It should be understood, however, that the application is not limited to the precise arrangements and instrumentalities shown. In the drawings.

DETAILED DESCRIPTION OF THE INVENTION

As used herein, the singular forms "a," "an," and "the" include plural referents, and plural forms include the singular referent unless the context clearly dictates otherwise.

Certain terminology is used in the following description for convenience only and is not limiting. Words designating direction such as "bottom," "top," "left," and "right" designate directions in the drawings to which reference is made, but are not limiting with respect to the orientation in which the preferred invention and its components and apparatus may be used. The terminology includes the words specifically mentioned above, derivatives thereof, and words of similar import.

As used herein, the term "about" with respect to any numerical value, means that the numerical value has some reasonable leeway and is not critical to the function or operation of the component being described or the system or subsystem with which the component is used. In the event that greater precision is required based on a particular situation, "about" and words of similar import, when used with a numerical value will include values within plus or minus 10% of the stated value.

As used herein, the term "substantially" with respect to any numerical value or description of any element or parameter means precisely the value or description of the element or parameter but within reasonable industrial manufacturing tolerances that would not adversely affect the function of the element or parameter or apparatus containing it, but such that variations due to such reasonable industrial manufacturing tolerances are less than the variations described as being "about."

In the following description, the terms "distal" and "proximal" are intended to be spatial orientation descriptors relative to the longitudinal axis of the vascular access device. Thus, a "proximal" end refers to an end of an element generally facing a medical professional and away from the patient and, conversely, a "distal" end refers to an end of an element generally facing away from the medical professional and toward the patient. Likewise a pair of elements described as "proximal" and "distal" elements are understood to have the same spatial relationship as described hereinabove for the ends of an element.

Generally, the preferred handheld vascular access device of the present invention is a device for providing vascular access rapidly and without the need for additional guidance or monitoring systems, such as an ultrasound system. With the preferred inventive handheld vascular access device, vascular access may be achieved by medical professionals in the field or other settings where conditions for practicing standard vascular access techniques, such as the Seldinger technique with a needle guidance system, may be impractical or impossible.

Referring to FIGS. 1-6, in a first preferred embodiment, a handheld vascular access device 10 includes a hub 12, a plurality of hollow access needles 14 fixedly attached to the hub 12, and a removable manifold 16 removably engageable with the hub 12. The hollow access needles 14 may be any of various cannulas, trocars, and the like typically used for accessing blood vessels or internal organs, and all are encompassed by the terms "hollow access needle," "aspirating needle" or sometimes, just "needle." The plurality of hollow access needles 14 are configured in such a way as to be in fluid communication with the hub 12, specifically with a plurality of ports 18 located within the hub 12. The plurality of hollow access needles 14 can be and preferably are evenly spaced at a distance $d_1$, $d_2$ from adjacent needles 14 (center of needle to center of needle), and provide optimized lateral spanning of the region of a desired blood vessel (such as the femoral artery). The handheld vascular access device 10 may be advanced in a controlled manner by a medical professional such that the hollow access needles 14 simultaneously and evenly penetrate the skin of the patient. Rather than being required to be inserted at a fixed angle relative to a patient's skin, typically about forty-five degrees (45°), as is typical in the prior art, a benefit of the preferred handheld vascular access device 10 of the present invention is that the device 10 can be held at any desired angle Δ relative to a surface patient's skin S to gain access to any desired blood vessel and can be adapted for insertion not only into a particular blood vessel, typically the femoral artery or vein, but also other blood vessels in other parts of the patient's body, such as, for example, the brachial artery or vein near a patient's shoulder or a radial artery or vein in a patient's arm. After one of the needles 14 strikes a vessel, it may be easier to advance the needle 14, with or without a guidewire 9 inserted through the hollow needle 14, if the angle Δ of the needle 14 relative to the skin surface S is made slightly more acute. For example, although the vessel is often initially accessed at an angle Δ of about forty-five degrees (45°) between the needle 14 and the skin surface S, further advancement of the needle 14 or a guidewire 9 inserted through the hollow access needle 14 at a more shallow angle Δ, such as, without limitation, an angle Δ of about thirty degrees (30°), while maintaining the position of the tip 14a of the needle 14 in the blood vessel. The ability to readily manipulate the preferred handheld vascular access device 10 of the present invention and the angle Δ relative to the skin surface S at limitless different angles and over different parts and areas of a patient's body, with their associated contours, is an improvement and an advantage of the present invention.

The handheld vascular access device 10 is used to obtain entry into a patient's vasculature, preferably the patient's aorta, the common iliac arteries or related relatively large vessels. The preferred vascular access device 10 includes the hub 12, the plurality of hollow access needles 14 fixedly coupled to the hub 12 and extending from the hub 12 to penetrate the patient's skin S and a removable manifold 16 removably engageable with the hub 12 for flushing or aspirating the hollow access needles 14.

The vascular access device 10 may be advanced by the medical professional until aspiration of blood into a lumen 44 of one of the needles 14 sufficient to indicate vascular access is observed emanating through the lumen 44 and into one of the ports 18. In the first preferred embodiment, the ports 18 include a first port 18a, a second port 18b and a third port 18c, with the second portion 18b positioned between the first and third or outside ports 18a, 18c. Access is gained by positioning the tip 14a of at least one of the needles 14 in the vessel such that blood flows into the associated lumen 44. If more than one needle 14 and port 18 is aspirating blood, the needle 14 and port 18 aspirating the most blood has likely accessed a large artery, e.g., the femoral artery, and is the access blood vessel of choice. Less aspiration would likely be noted in a smaller artery or vein. The guidewire 9 may then be fed through the lumen 44 of the aspirating port 18, the lumen 44 of the needle 14 and into the blood vessel. The handheld vascular access device 10 may then be removed from the blood vessel over the guidewire 9 while maintaining the position of the guidewire 9 in the blood vessel. The desired blood vessel is thus accessed and ready to have a catheter, sheath, occlusion device, second wire, or other medical device inserted therein, as necessary, over the guidewire 9. The guidewire 9 may subsequently be removed from the vessel to continue the procedure. By use of the preferred inventive handheld vascular access device 10, vascular access may rapidly, safely, and repeatedly be achieved, without the need for additional monitoring or guidance systems and without the need for guides that pre-set an insertion angle for the vascular access device 10. As such, vascular access may be achieved by medical professionals in the field or other settings, where conditions for practicing standard vascular access techniques with a needle guidance system or guide may be impractical or impossible or the medical technician desires relatively quick and simple access to the vessel.

Figure 2A:
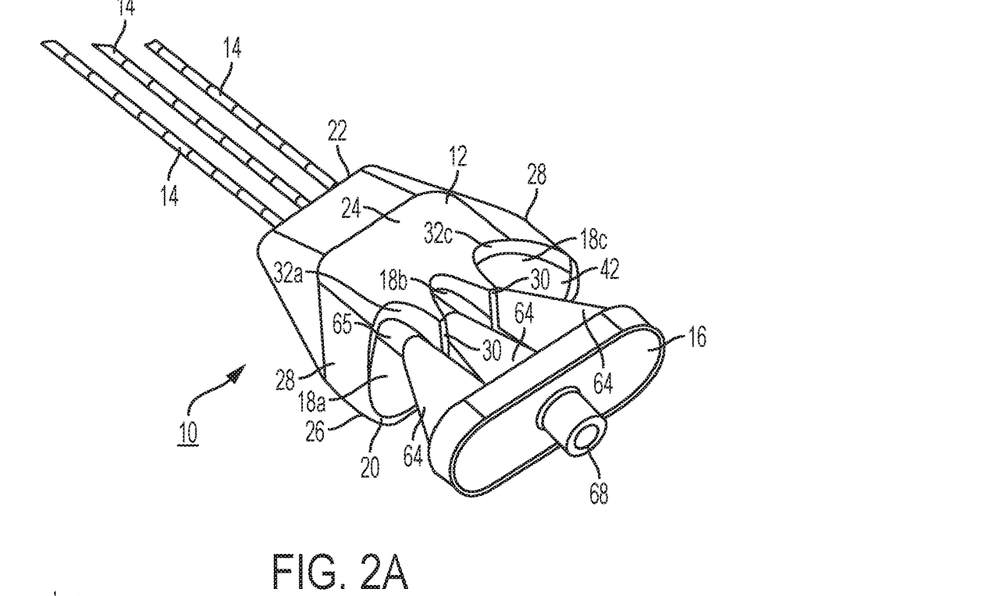
FIG. 2A is a partially exploded top isometric view of a proximal portion of the vascular access device of FIG. 1.
Figure 2B:
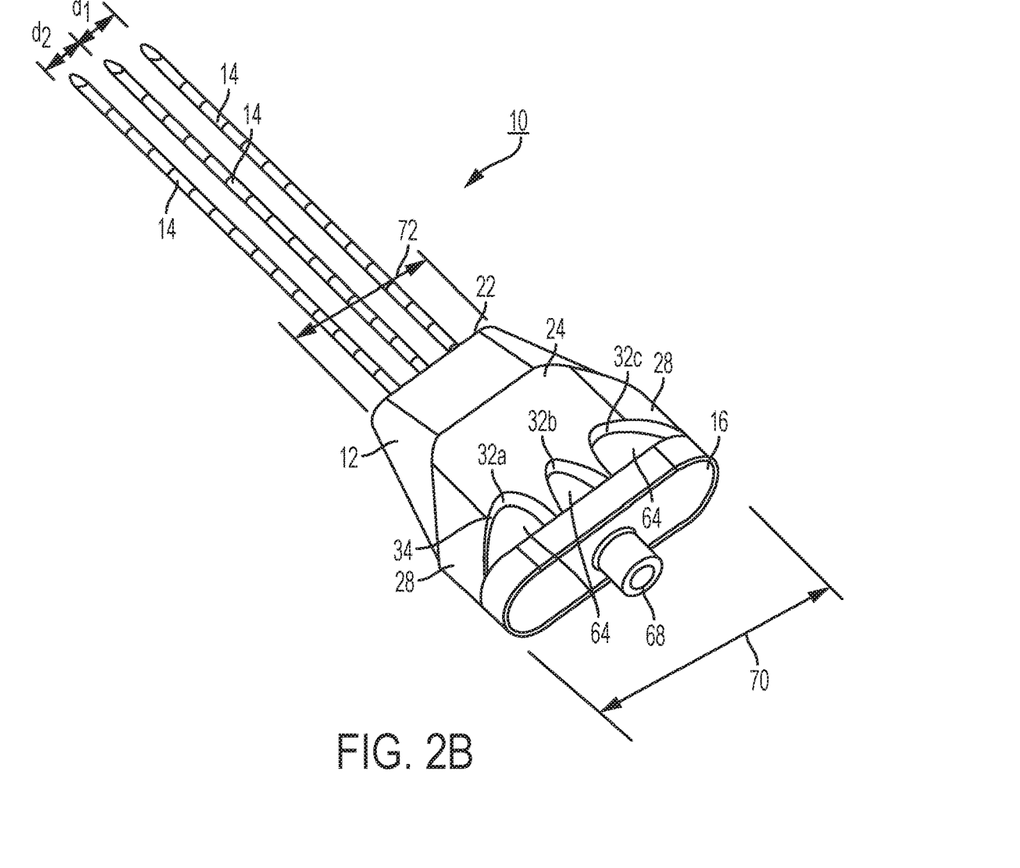
FIG. 2B is a top assembled isometric view of the handheld vascular access device of FIG. 1.

Referring to FIGS. 2A and 2B, the hub 12 has a proximal end 20 and a distal end 22 with the distal end 22 disposed opposite the proximal end 20 and toward the patient during use. Further, the hub 12 includes a top wall 24, a bottom wall 26, and side walls 28. The side walls 28 connect the top wall 24 to the bottom wall 26 and extend between the proximal end 20 of the hub 12 and the distal end 22 of the hub 12. The hub 12 also includes at least one inner wall 30, preferably two (2) inner walls 30, extending between the proximal end 20 and distal end 22. The inner walls 30 preferably define the plurality of ports 18. In the first preferred embodiment, as best shown in FIG. 2A, there are two (2) inner walls 30, resulting in three (3) ports 18, including the first, second and third ports 18a, 18b, 18c, that correspond to the three (3) needles 14 extending from the distal end 22 of the hub 12.

A plurality of recesses 32, including first, second and third recesses 32a, 32b, 32c, are disposed within the top wall 24 and are positioned along the proximal end 20 of the hub 12. The recesses 32 are aligned with the ports 18, preferably have a generally arcuate or U-shape and extend from the proximal end 20 towards the distal end 22 of the hub 12. The recesses 32 preferably form arcuate profiles 34 within the top wall 24 and the bottom wall 26 preferably does not include counterpart recesses. The first recess 32a preferably opens into the first recess 18a, the second recess 32b preferably opens into the second recess 18b and the third recess 32c preferably opens into the third recess 18c. The first and third recesses 32a, 32c are preferably outside recesses 32a, 32c, are substantially mirror images of each other, extend relatively wide relative to a center of the hub 12 and, therefore, are larger than the second or central recess 32b. In the first preferred embodiment, the arcuate profiles 34 are substantially U-shaped; but may be any shape such as a semi-circle, triangle, parallelepiped or any other shape that allows access to the ports 18 from above or at an angle relative to the top wall 24, such as access by insertion of the guidewire 9 substantially perpendicularly relative to the top wall 24 into the recesses 32. The recesses 32 facilitate the loading of the guidewire 9 into the hub 12 by a medical professional after arterial or venous vasculature has been achieved or before access is achieved, such that the guidewire 9 need not be axially aligned with the needles 14 or ports 18, but may be align linearly or angled into the ports 18 from above and behind the handheld vascular access device 10.

Figure 3:
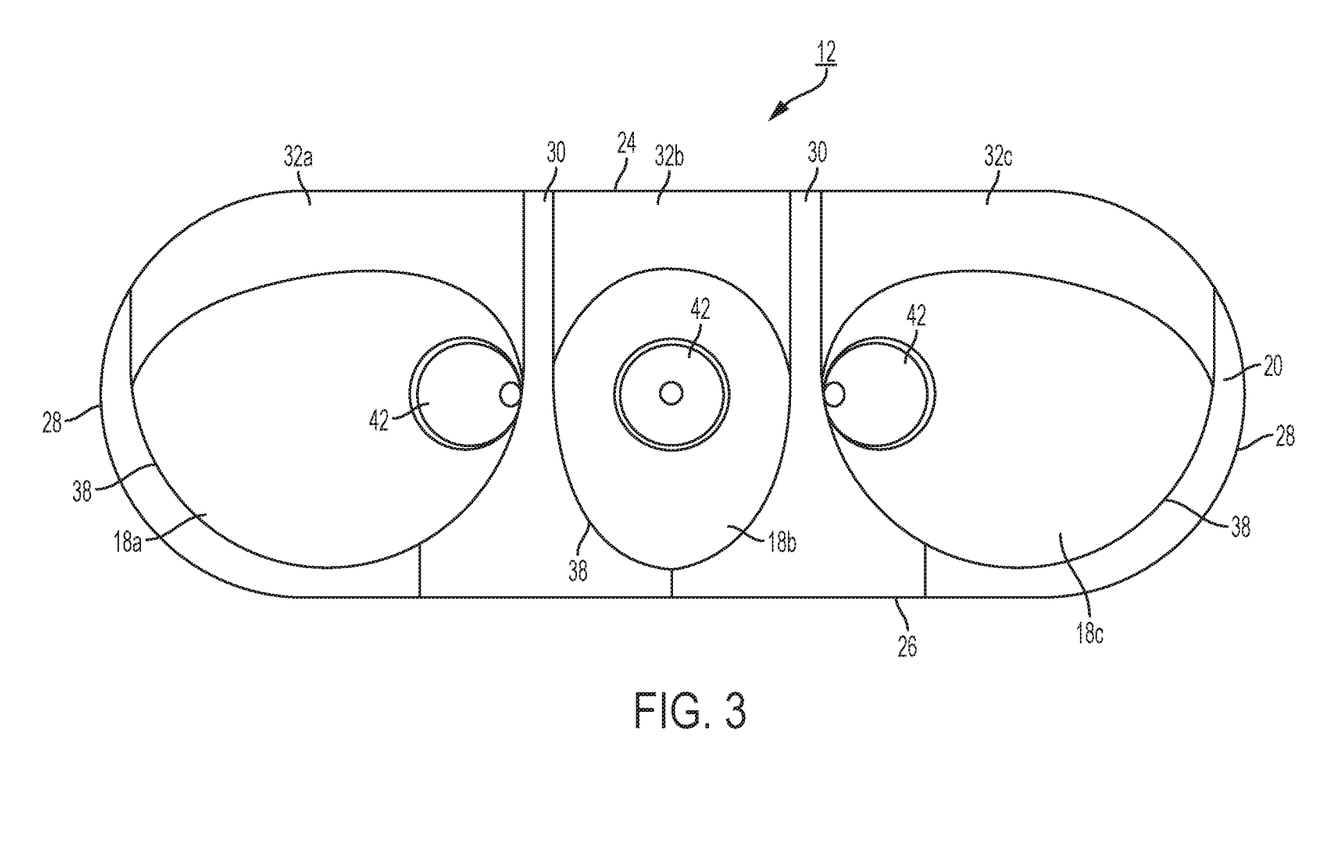
FIG. 3 is a front or proximal end elevational view of a hub of the handheld vascular access device of FIG. 1.

Referring to FIGS. 2A-3, each of the plurality of ports 18 has a proximal port end 38 that defines a proximal port cross-sectional area 39 and a distal port end 42 that defines a distal port cross-sectional area 43. The proximal port cross-sectional area 39 includes a first proximal port end cross-sectional area 39a associated with the first port 18a, a second or central proximal port end cross-sectional area 39b associated with the second port 18b and a third proximal port end cross-sectional area 39c associated with the third port 18c. The first and third proximal port end cross-sectional areas 39a, 39c have a relatively wide oval-shape, are substantially mirror images of each other and are positioned laterally relative to the second or central proximal port end cross-sectional area 39b. The second proximal port end cross-sectional area 39b is smaller than the first and second proximal port end cross-sectional areas 39a, 39c and has a relatively tall oval-shape. The distal port cross-sectional area 43 includes first, second and third distal port end cross-sectional areas 43a, 43b, 43c associated with the first, second and third ports 18a, 18b, 18c, respectively. The distal port cross-sectional areas 43a, 43b, 43c are preferably circular and have substantially the same size, but are not so limited and may have other shapes and sizes, such as oval. The distal port cross-sectional areas 43a, 43b, 43c may also change in dimension as they extend closer to the proximal ends of the needles 14, but preferably have a dimension that accepts the proximal end of the needle 14 therein to secure the needle 14 to the hub 12. The first, second and third distal port end cross-sectional areas 43a, 43b, 43c are each smaller than the first, second and third proximal port end cross-sectional areas 39a, 39b, 39c to facilitate the tapering of the first, second and third ports 18a, 18b, 18c for ease of insertion of the guide wire 9 during use.

Figure 3A:
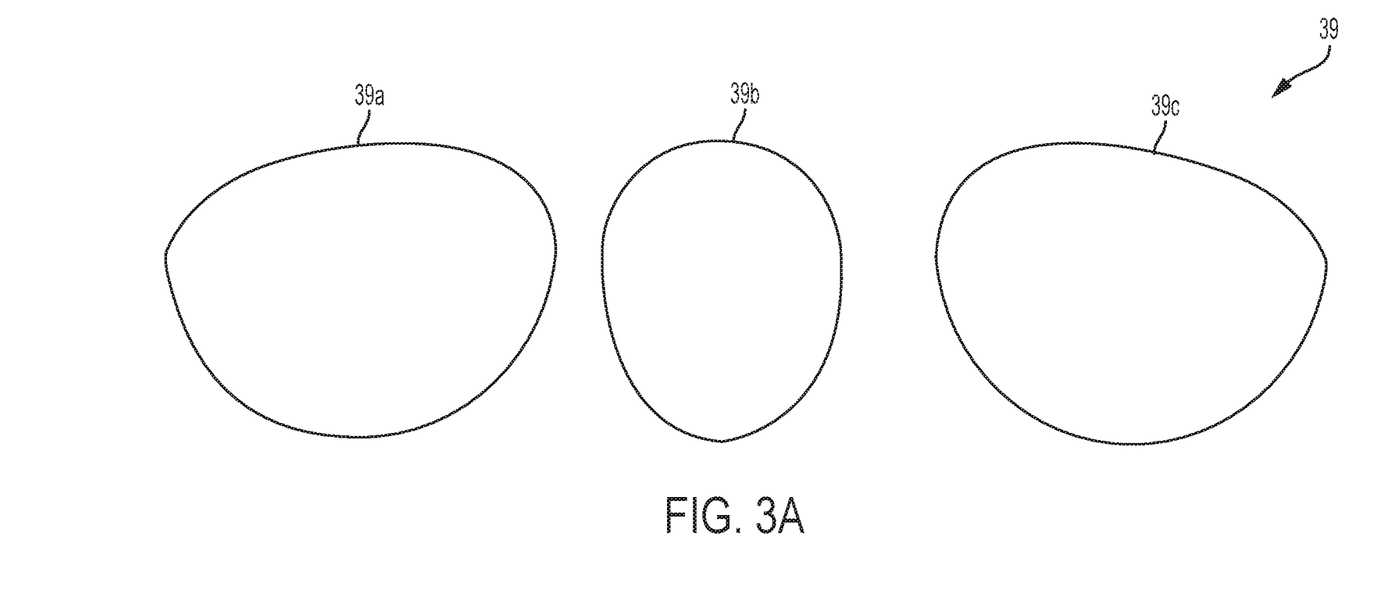
FIG. 3A is a cross-sectional view of ports at proximal port ends of the hub of FIG. 3.
Figure 3B:
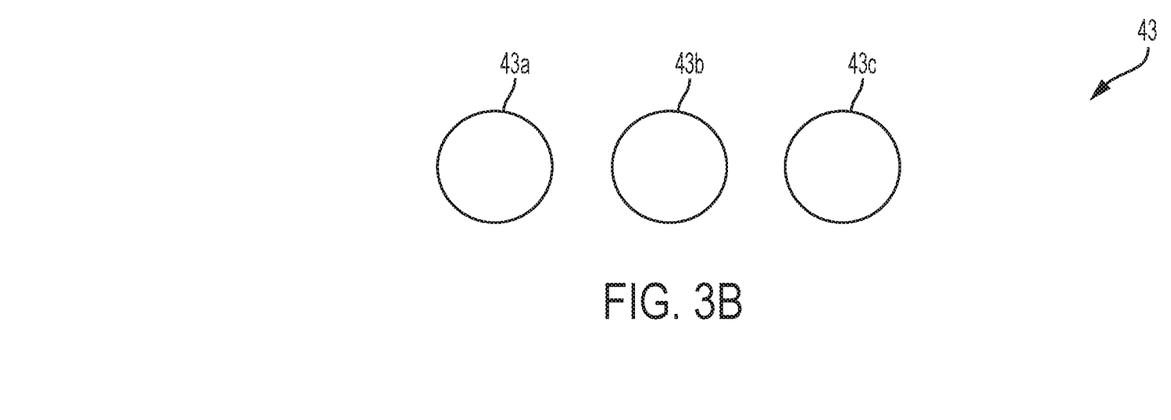
FIG. 3B is a cross-sectional view of ports at distal port ends of the hub of FIG. 3

The ports 18 taper from the proximal port cross-sectional areas 39 defined at the proximal port end 38 to the distal port cross-sectional area 43 defined at the distal port end 42. The distal port cross-sectional areas 43 are smaller than the proximal port cross-sectional areas 39 such that the guidewire 9 is relatively easily inserted into the ports 18 and the ports 18 guide the guidewire 9 into the lumen 44 of each of the needles 14, respectively. This taper of the ports 18 can be in any geometric form, but in the first preferred embodiment, the ports 18 have a truncated conical geometry. Each of the plurality of ports 18 does not necessarily have the same geometry. For example, central port 18 of the first preferred embodiment has a relatively narrow geometry in comparison to the outside ports 18, which extend laterally in a relatively wide configuration and are substantially mirror images of each other. The geometry of the ports 18 allow for easier access of the guidewire 9 into the needle 14 through the larger proximal port cross-sectional areas 39 of the proximal port ends 38. The geometry of the ports 18 also allows for less restrictive flow of any fluid that may travel through the needle 14 into the hub 12 from the distal port end 42 of the ports 18 and through the port 18 to the proximal port ends 28. The fluids may include blood, a flushing saline fluid, medicines or other related fluids that may be utilized in procedures associated with the vascular access device 10.

The hub 12 of first preferred handheld vascular access device 10 has a first width 70 at the proximal end 20 and a second width 72 at the distal end 22. The second width 72 is preferably smaller than the first width 70 to provide visualization for the user at the distal end 22 and to limit interference with the patient's skin S. The side walls 28 and top wall 24 preferably taper between the proximal and distal ends 20, 22 to define the first width 70 and the second width 72. The first and second widths 70, 72 also accommodate the tapering or conical shape of the ports 18 that have the wider proximal port ends 38 than their distal port ends 42.

Figure 1:
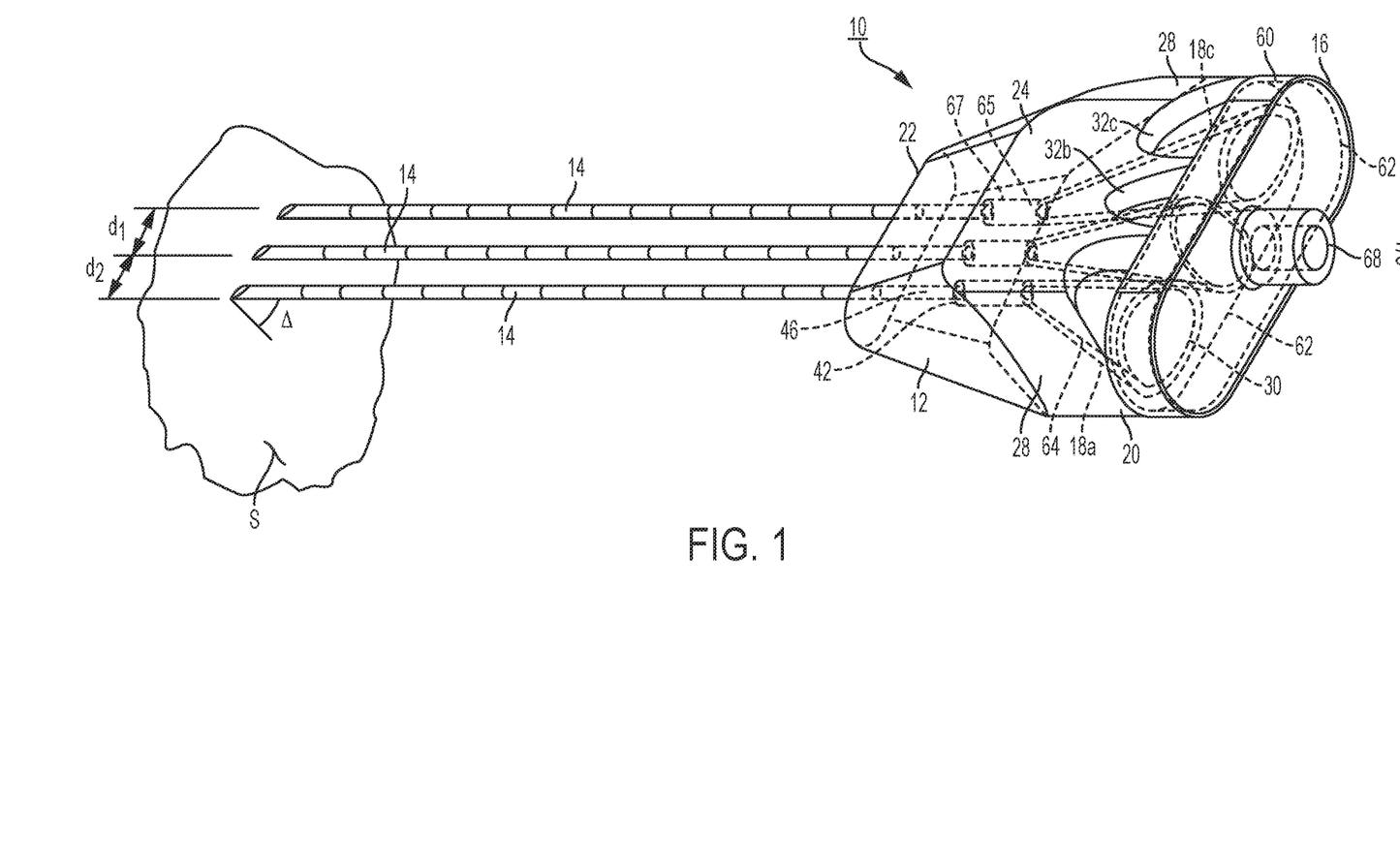
FIG. 1 is a top isometric view of a handheld vascular access device in accordance with a first preferred embodiment of the present invention, with certain internal aspects shown in phantom lines.
Figure 4:
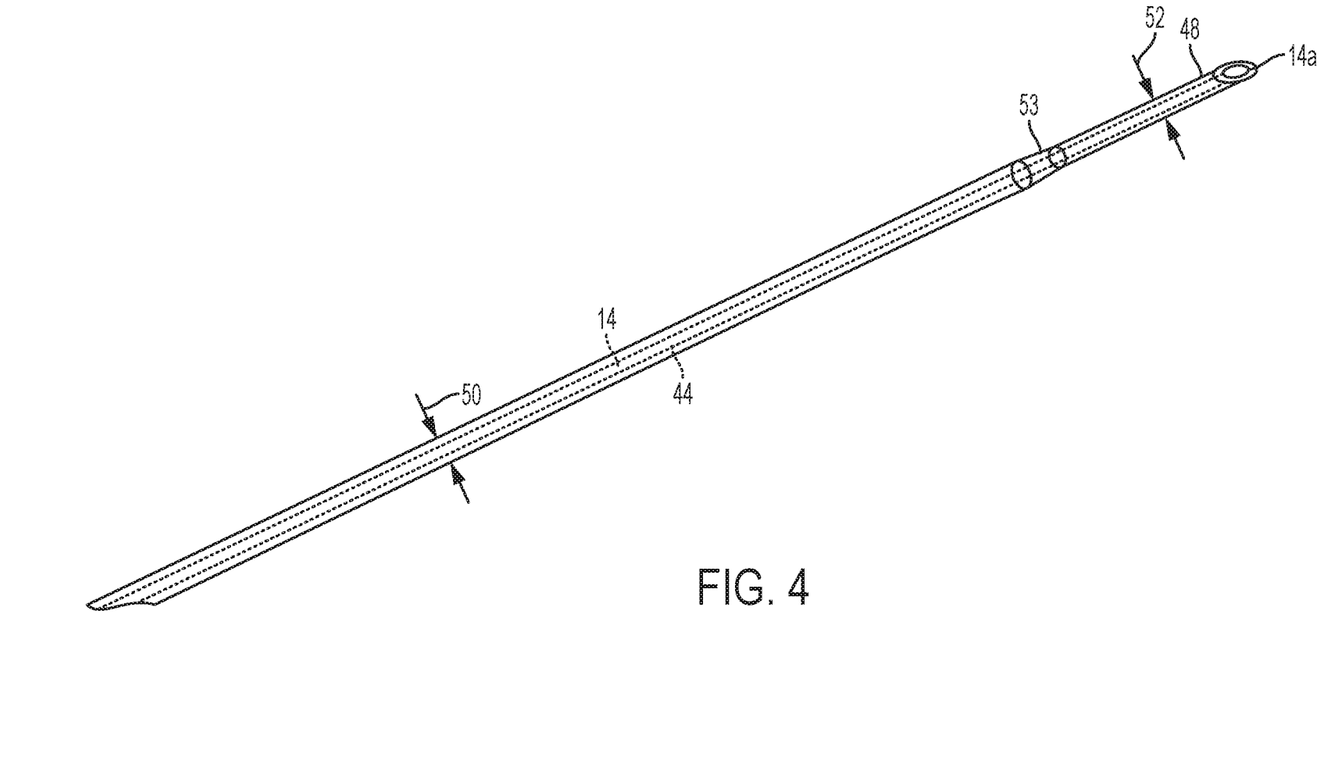
FIG. 4 is a top isometric view of a distal portion of a hollow access needle of the handheld vascular access device of FIG. 1, wherein phantom lines show the needle's lumen according to a first preferred embodiment of the present invention.

Referring to FIGS. 1 and 4, each of the plurality of hollow access needles 14 includes the lumen 44 that extends between a first proximal end 46 (identified in FIG. 1) and a second distal end 48 or to the tip 14a. The second distal end 48 of the needle 14 forms the sharp tip 14a, such as in a trocar, for piercing the skin S and blood vessel. The lumen 44 allows for fluid communication between each of the plurality of ports 18 of the hub 12 and the local vasculature, respectively, when the tip 14a of the needle 14 is positioned in the vasculature. Further, the needles 14 preferably have a first needle diameter 50 near the first proximal end 46 or along a first proximal section and a second needle diameter 52 at the second distal end 48 or along a distal section. A tapered section 53 connects the first diameter 50 of the proximal section to the second diameter 52 of the distal section. The larger second needle diameter 50 makes the needle 14 more robust, stiffer and stronger, since it typically has the greater length compared to the length of the smaller first needle diameter 52, and is fixedly coupled or connected at the first proximal needle end 46 to the distal end 42 of the port 18 of the hub 12. The second needle diameter 52 is preferably less than the first needle diameter 50, so as to minimize to puncture size at the skin S and vasculature and to reduce impact on the patient's body. The second needle diameter 52 is also preferably sized smaller than the first needle diameter 50 to potentially limit the pain experienced by the patient during insertion of the smaller second needle diameter 52 into the skin surface S.

Figure 5:
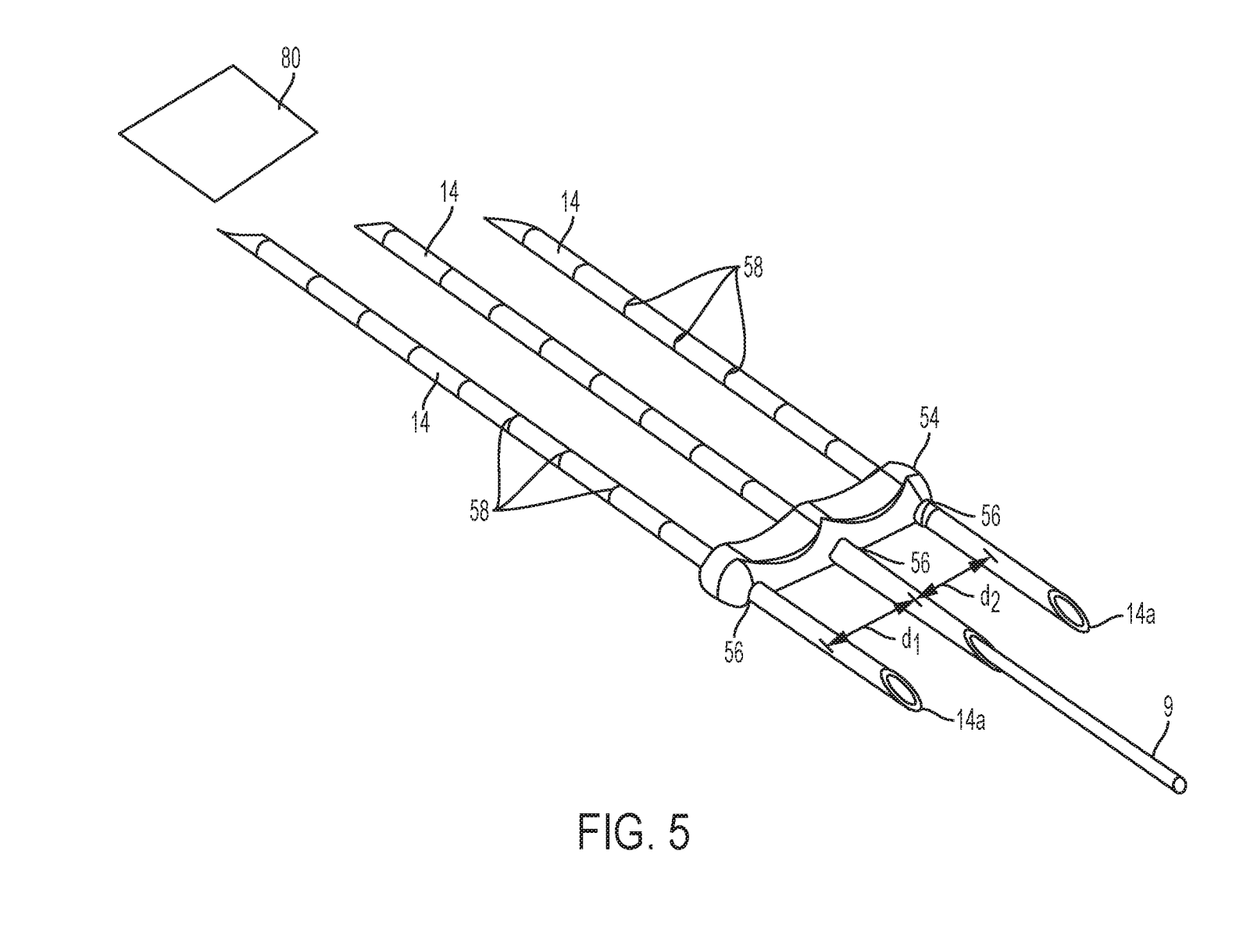
FIG. 5 is a top isometric view of a distal portion of a plurality of hollow access needles with a spacer member that may be utilized with the vascular access device of FIG. 1.

Referring to FIG. 5, the handheld vascular access device 10 preferably includes the three (3) hollow access needles 14, but may comprise any number of needles 14, such as two (2), four (4) or more, so as to maximize the probability of entering the desired artery or vein on a first attempt. The plurality of hollow access needles 14 are preferably aligned in or arranged along a needle plane 80 and have their axes aligned substantially parallel to one another. As mentioned above, the hollow access needles 14 may be spaced evenly from each other by the first and second distances $d_1$, $d_2$, but are not necessarily evenly spaced from each other. The center-to-center spacing of the needles 14 can be different based on clinician, patient or procedure requirements, with different intended uses for accessing different vessels. The center-to-center needle spacing or first and second distances $d_1$, $d_2$ may be about one millimeter (1 mm) to about ten millimeters (10 mm), preferably about three millimeters (3 mm) to about five millimeters (5 mm), and more preferably, about five millimeters (5 mm), in the first preferred embodiment. To achieve the desired alignment, the handheld vascular access device 10 further includes a spacer member 54 having apertures 56 through which the hollow access needles 14 pass and may slide with a friction fit. The apertures 56 are preferably cylindrical and sized to receive the proximal or distal diameters 50, 52 of the needles 14. The spacer member 54 serves to maintain the parallel spacing of the hollow access needles 14 and can be moved along at least a portion of the axial length of the needles 14 as desired to maintain the desired alignment.

Additionally, at least one of the hollow access needles 14 preferably includes distance markings 58 along the length of the outer surface of the needle 14. The distance markings 58 are set at predetermined ascending distances along the length of the needle 14 from the second distal end 48 or tips 14a to the first proximal end 46. These markings 58 are to assist the medical professional in determining the depth to which the vascular access device 10, specifically, the individual needles 14, has advanced into the patient. The markings 58 have predetermined distances from about one millimeter (1 mm) to about ten millimeters (10 mm), preferably about five millimeters (5 mm), and can have engraved rings or transverse lines on their upper surfaces or around the full diameter of their outer surfaces that are visible to the medical person using the device 10. The markings 58 can and preferably also include numerical values notifying the user of the depth of the tips 14a in the patient during use.

Referring to FIGS. 1-6B, the handheld vascular access device 10 includes the removable manifold 16 which has a housing 60. The housing 60 includes an internal cavity 62 and a plurality of projections 64 matching the number of the plurality of ports 18 in the hub 12. Each of projections 64 extend distally from a distal face of the housing 60 and are each alignable with a port 18 of the hub 12. Each projection 64 is tapered and has a geometry to match the aligned port 18, such that the projections 64 align with the ports 18 of the hub 12 in an assembled configuration. In the first preferred embodiment shown in FIGS. 6A and 6B, each projection 64 has a distal end 65 that can preferably be a male luer fitting. Preferably, the projections 64 have a truncated conical geometry matching the truncated conical geometry of the ports 18 in the hub 12, as was described above. Further, each projection 64 includes a projection lumen 66 extending between the internal cavity 62 and the distal end of the projection 64. Each projection lumen 66 is in fluid communication with the internal cavity 62, the aligned port 18 and the lumen 44 of the aligned needle 14, so that blood or other fluid can flow from any of the needles 14 into the internal cavity 62 of the manifold 16. In this first preferred embodiment, each of the ports 18 has a distal female fitting 67 (best seen in FIG. 1), preferably a female luer fitting. It is preferred that the projections 64 with their distal male luer fittings 65 mate with the aligned female luer fittings 67 of the hub ports 18. The manifold 16 of the first preferred embodiment is retained together with the hub 12 so as to be removably engaged with a friction fit to prevent leaks of blood or other fluid between the hub 12 and the manifold 16.

Figure 6A:
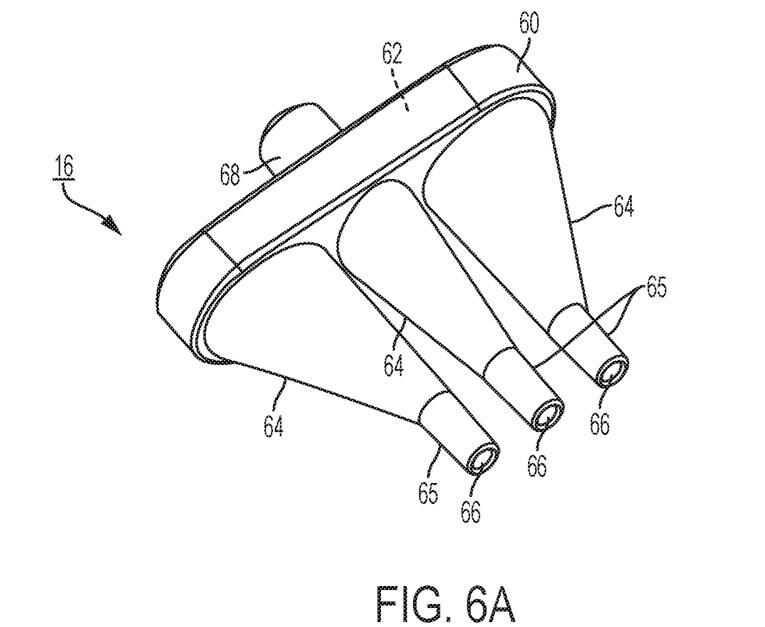
FIG. 6A is a top isometric view of the manifold of the handheld vascular access device of FIG. 1.
Figure 6B:
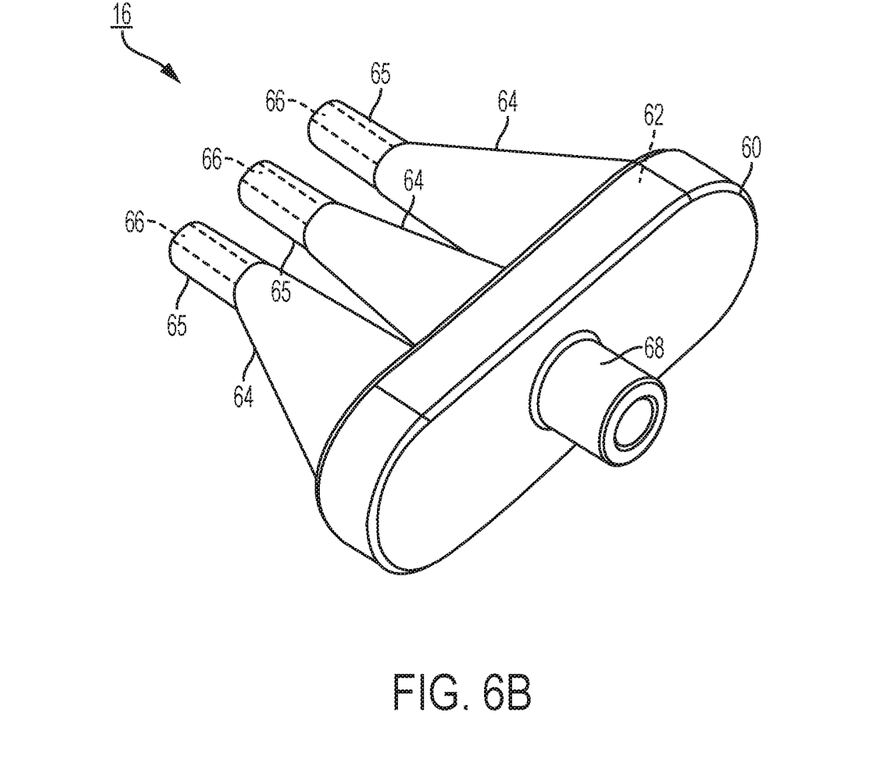
FIG. 6B is an alternative top isometric view of the manifold of the handheld vascular access device of FIG. 1.

The removable manifold 16 further includes a fluid connector 68 which extends proximally from the proximal face of the housing 60 and is in fluid communication with the internal cavity 62. The removable manifold 16 allows the medical professional to both flush the needles 14 and hub 12 as well as to aspirate the needles 14 during use (i.e. maintain a negative pressure within the needles 14 so that fluid may travel quickly from the second distal end 48 of the needles 14 to the hub 12). Further, the fluid connector 68 of the removable manifold 16 allows connection to a standard syringe or other similar medical device, such as a luer fitting, which may be either a friction fit, sometimes called a luer slip fit, resulting in a friction fit, or a more positive locking fitting, such as a fitting that may be at least partially screwed together, for instance a luer lock or Luer Lok® fitting, to engage the vascular access device 10 while the device 10 is being used. In a preferred embodiment, the hub 12 and manifold 16 are constructed of a transparent, translucent or semi-transparent and biocompatible material, such as polyethylene, nylon, polycarbonate, and the like, such that fluid aspiration will be readily visible in the ports 18 even when the removable manifold 16 is engaged with the hub 12.

Referring to FIGS. 1-2B, 3A, 3B, 6A and 6B, in the first preferred embodiment, each of the plurality of ports 18 has a first or proximal port end cross-sectional area 39a, 39b, 39c at the proximal port end 38 and a second or distal port end cross-sectional area 43a, 43b, 43c at the distal port end 42. Each of the plurality of ports 18 tapers from the first or proximal port end cross-sectional area 39a, 39b, 39c to the second or distal port end cross-sectional area 43a, 43b, 43c. The manifold 16 includes the housing 60 with the internal cavity 62. The manifold 16 further includes the plurality of projections 64 extending distally from the housing 60. Each of the plurality of projections 64 is aligned with one of the plurality of ports 18. Each of the plurality of projections 18 is tapered to substantially match the taper of an aligned port 18 of the plurality of ports 18, respectively, and is removably engageable with the ports 18 in a friction fit. Each of the plurality of projection 64 has a projection lumen 66. Each of the projection lumens 66 extends between the internal cavity 62 of the housing 60 to the distal end of the projection 64. The manifold 16 also includes the fluid connector 68 extending proximally from the housing 60. The fluid connector 68 is in fluid communication with the internal cavity 62, such that fluid is able to flow through the fluid connector 68, through the internal cavity 62 and out of the projection lumens 66.

Figure 7:
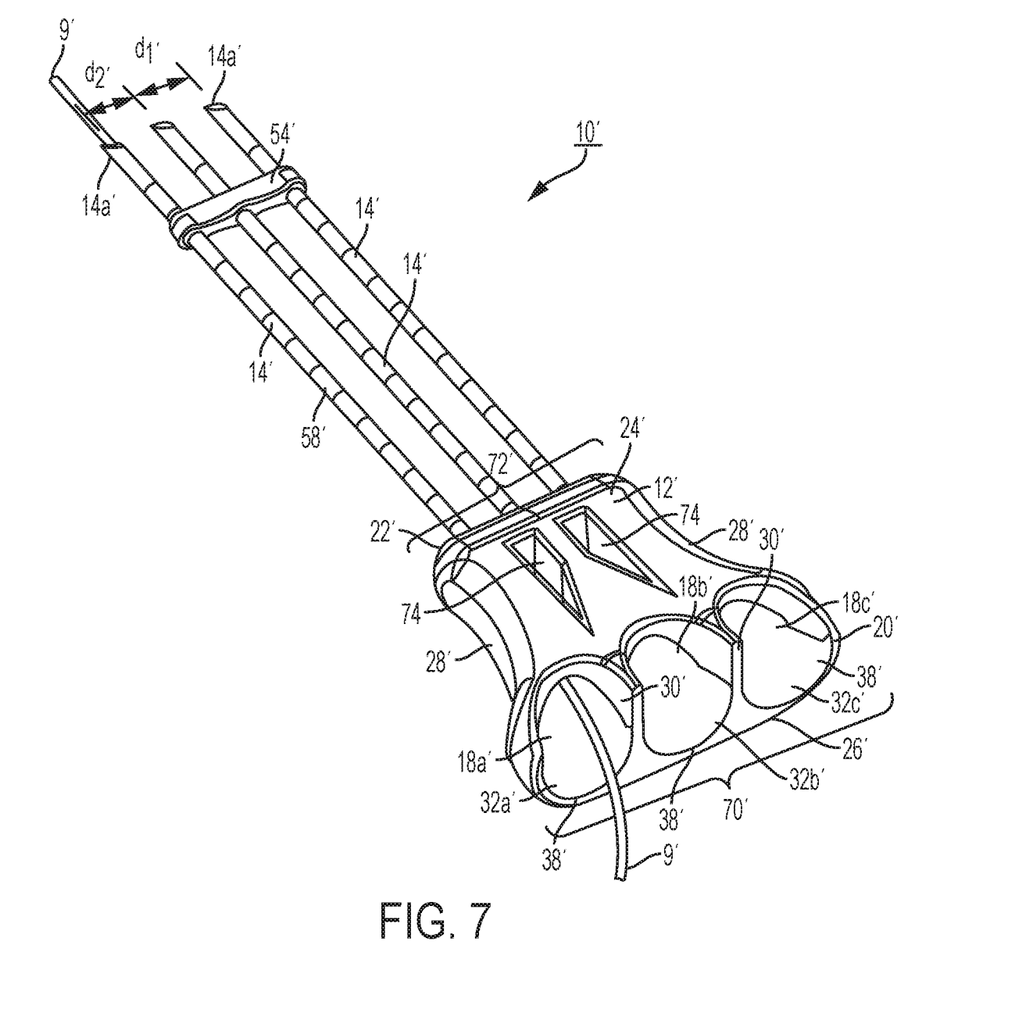
FIG. 7 is top isometric view of a handheld vascular access device in accordance with a second preferred embodiment of the present invention.
Figure 8:
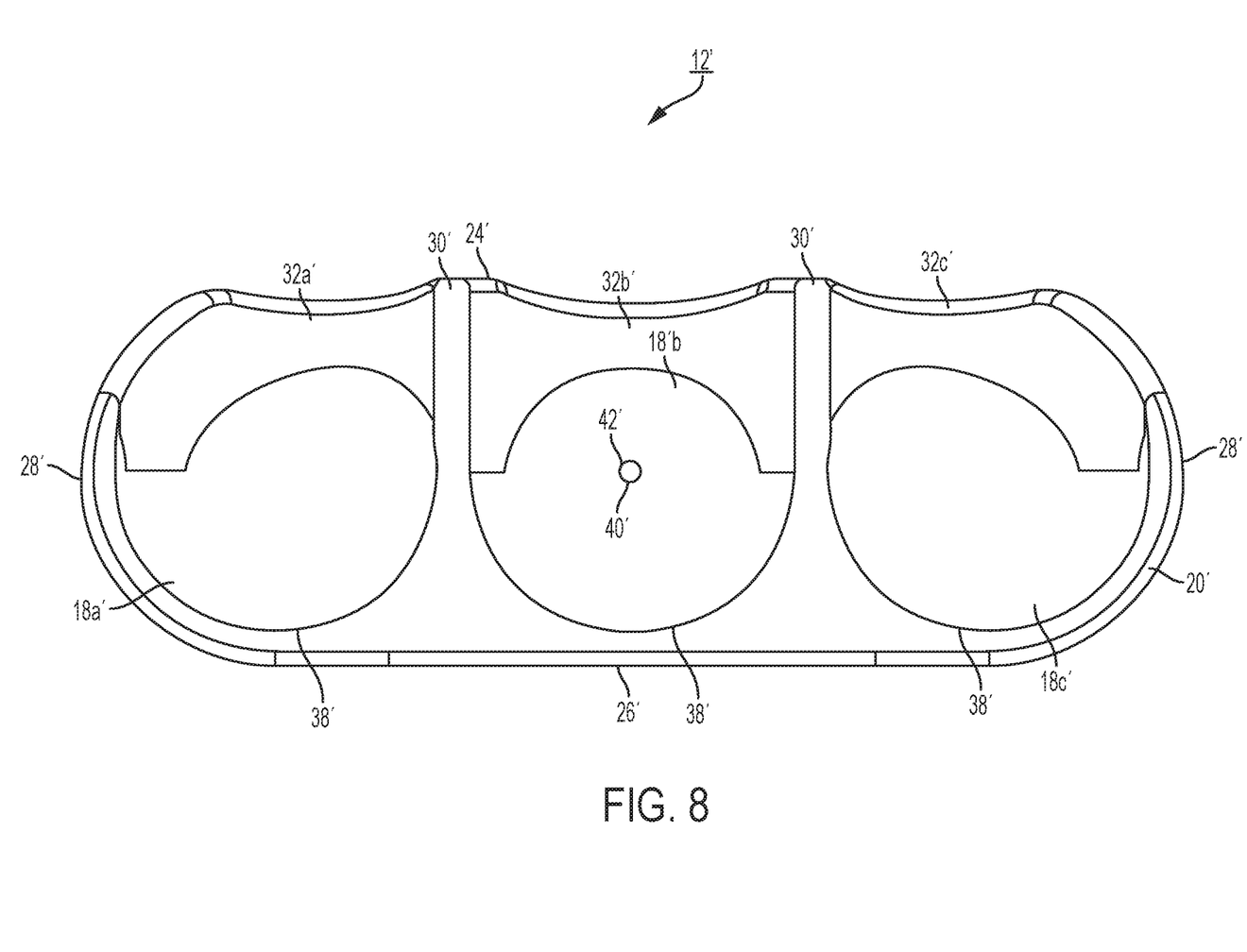
FIG. 8 is a front or proximal end elevational view of the vascular access device of FIG. 7.

Referring to FIGS. 7 and 8, in a second preferred embodiment of a handheld vascular access device 10', the hub 12' has a first width 70' at the proximal end 20' and a second width 72' at the distal end 22'. The second preferred handheld vascular access device 10' has similar or the same features as the first preferred vascular access device 10 and the same reference numbers are utilized to identify the features of the second preferred embodiment with a prime symbol ("'") utilized to distinguish the features of the second preferred access device 10' from the first preferred access device 10. The second width 72' in the second preferred embodiment is smaller than the first width 70'. Additionally, the side walls 28' extend concavely to taper from the first width 70' to the second width 72' between the proximal end 20' and the distal end 22'. This second preferred embodiment, accordingly, has a diminishing profile moving distally away from the medical professional towards the patient during use and when the tips 14a' are positioned proximate the skin surface S. The reduced profile of the hub 12' allows the medical professional greater visibility when utilizing the vascular access device 10' of the second preferred embodiment to increase efficiency of vasculature access and allows a different and potentially improved grip of the sides 28' of the hub 12' during use. Further, the hub 12' includes a plurality of openings 74 which extend at least partially from either the top wall 24' or the bottom wall 26' in the direction of the opposite surface. In the second preferred embodiment, the openings 74 extend completely between the top wall 24' and the bottom wall 26'. The removal of the hub 12' material by way of the openings 74 serves to maintain a center of gravity of the handheld vascular access device 10' towards the distal end of the device 10' and reduces the amount of material needed to construct or mold the device 10'.

It will be appreciated by those skilled in the art that changes could be made to the preferred embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A handheld multi-needle vascular access device for gaining access to a patient's vessel, the access device comprising:
    a discrete hub having a proximal end, a distal end disposed opposite the proximal end, a top wall, a bottom wall disposed opposite the top wall and side walls connecting the top wall and the bottom wall, the side walls extending between the proximal end and the distal end, an inner wall extending between the proximal end and the distal end, the inner wall and side walls defining a plurality of ports extending from the proximal end to the distal end, each of the plurality of ports having a proximal port end and a distal port end, the proximal port ends defining a proximal port end cross-sectional area and the distal port ends defining a distal port end cross-sectional area, the proximal port end cross-sectional areas being greater than the distal port end cross-sectional areas, each of the plurality of ports tapering from the proximal port end to the distal port end;
    a plurality of hollow access needles arranged along a plane and fixedly coupled to the distal end of the hub, each of the plurality of needles having a proximal needle end fixedly coupled to the distal end of the hub and a tip disposed distally of the proximal needle end; and
    a manifold independently engageable with the plurality of ports of the hub via a friction fit and disengageable therefrom, the manifold including a housing with an internal cavity, the internal cavity being in fluid communication with the plurality of ports when the manifold is engaged with the hub.

2. The vascular access device of claim 1, wherein the plurality of ports include a first port, a second port and a third port, the second port positioned between the first and third ports.

3. The vascular access device of claim 2, wherein the first port has a first proximal port end cross-sectional area and the second port includes a second port end cross-sectional area, the first port end cross-sectional area being greater than the second port end cross-sectional area.

4. The vascular access device of claim 2, wherein the first port has a first distal port end cross-sectional area, the second port has a second distal port end cross-sectional area and the third port has a third distal port end cross-sectional area, the first, second and third distal port end cross-sectional areas being substantially the same.

5. The vascular access device of claim 1, wherein the plurality of hollow access needles are oriented substantially parallel relative to each other.

6. The vascular access device of claim 5, wherein each of the plurality of hollow access needles is spaced apart from an adjacent hollow access needle a distance of approximately one to ten millimeters (1-10 mm).

7. The vascular access device of claim 1, wherein each needle of the plurality of hollow access needles includes a lumen extending between the first proximal needle end and the tip, each of the lumens being in fluid communication with the distal port end of one of the plurality of ports, respectively.

8. The vascular access device of claim 1, wherein at least one of the plurality of hollow access needles has a proximal diameter and a distal diameter, the distal diameter being smaller than the proximal diameter.

9. The vascular access device of claim 1, wherein at least one of the plurality of hollow access needles has distance markings on an outer surface spaced a predetermined distance apart.

10. The vascular access device of claim 1 further comprising:
    a spacer member having apertures through which the plurality of hollow access needles pass, respectively, to maintain a substantially parallel spacing of the plurality of hollow access needles from the proximal needle end to the tip.

11. The vascular access device of claim 1, wherein the manifold also includes a plurality of projections extending distally from the housing, each one of the plurality of projections being alignable with one of the plurality of ports.

12. The vascular access device of claim 11, wherein each of the plurality of ports has a proximal port end cross-sectional area at the associated proximal port end and a distal port end cross-sectional area at the associated distal port end, each of the plurality of ports taper from the first proximal port end cross-sectional area to the distal port end cross-sectional area, each of the plurality of projections having a taper to substantially match the taper of a corresponding one of the plurality of ports.

13. The vascular access device of claim 11, wherein the plurality of projections are configured for the friction fit into the plurality of ports, respectively.

14. The vascular access device of claim 11, wherein the manifold further includes a fluid connector extending proximally from the housing, the fluid connector being in fluid communication with the internal cavity.

15. The vascular access device of claim 1, wherein the plurality of ports includes a first port and a second port, the first port having a first proximal port end cross-sectional area defined at the proximal port end and the second port having a second proximal port end cross-sectional area defined at the distal port end, the first proximal port end cross-sectional area being greater than the second proximal port end cross-sectional area.

16. The vascular access device of claim 1, wherein the proximal end of the hub has a first width and the distal end of the hub has a second width, the second width being smaller than the first width.

17. The vascular access device of claim 16, wherein the side walls extend concavely between the proximal end towards the distal end.

18. A handheld multi-needle vascular access device for gaining access to a patient's vessel, the access device comprising:
- a hub having a proximal end, a distal end disposed opposite the proximal end, a top wall, a bottom wall disposed opposite the top wall and side walls connecting the top wall and the bottom wall, the side walls extending between the proximal end and the distal end, an inner wall extending between the proximal end and the distal end, the inner wall and side walls defining a plurality of ports extending from the proximal end to the distal end, each of the plurality of ports having a proximal port end and a distal port end, the proximal port ends defining a proximal port end cross-sectional area and the distal port ends defining a distal port end cross-sectional area, the proximal port end cross-sectional areas being greater than the distal port end cross-sectional areas, each of the plurality of ports tapering from the proximal port end to the distal port end;
- a plurality of hollow access needles arranged along a plane and fixedly coupled to the distal end of the hub, each of the plurality of needles having a proximal needle end fixedly coupled to the distal end of the hub and a tip disposed distally of the proximal needle end; and
- a removable manifold removably engages the hub at the proximal end of the hub,
- wherein the top wall includes a plurality of recesses disposed along the proximal end of the hub and aligned with the plurality of ports, the recesses extending from the proximal end of the hub toward the distal end of the hub.

19. The vascular access device of claim 18, wherein each recess forms an arcuate profile in the top wall.

20. A handheld multi-needle vascular access device for gaining access to a patient's vessel, the access device comprising:
- a hub having a proximal end, a distal end disposed opposite the proximal end, a top wall, a bottom wall disposed opposite the top wall and side walls connecting the top wall and the bottom wall, the side walls extending between the proximal end and the distal end, an inner wall extending between the proximal end and the distal end, the inner wall and side walls defining a plurality of ports extending from the proximal end to the distal end, each of the plurality of ports having a proximal port end and a distal port end, the proximal port ends defining a proximal port end cross-sectional area and the distal port ends defining a distal port end cross-sectional area, the proximal port end cross-sectional areas being greater than the distal port end cross-sectional areas, each of the plurality of ports tapering from the proximal port end to the distal port end;
- a plurality of hollow access needles arranged along a plane and fixedly coupled to the distal end of the hub, each of the plurality of needles having a proximal needle end fixedly coupled to the distal end of the hub and a tip disposed distally of the proximal needle end; and
- a removable manifold removably engages the hub at the proximal end of the hub,
- wherein the manifold includes a housing with an internal cavity, the manifold also includes a plurality of projections extending distally from the housing, each one of the plurality of projections being alignable with one of the plurality of ports, and
- wherein each of the plurality of projections include a projection lumen, each projection lumen extending between the internal cavity of the housing to a distal end of the respective one of the plurality of projections.

* * * * *